United States Patent
Yang et al.

(10) Patent No.: US 11,364,318 B2
(45) Date of Patent: Jun. 21, 2022

(54) OPTICAL STERILIZATION DEVICE

(71) Applicant: Lextar Electronics Corporation, Hsinchu (TW)

(72) Inventors: Chou-Hang Yang, Hsinchu (TW); Yi-Hsing Lee, Hsinchu (TW)

(73) Assignee: Lextar Electronics Corporation, Hsinchu (TW)

( * ) Notice: Subject to any disclaimer, the term of this patent is extended or adjusted under 35 U.S.C. 154(b) by 99 days.

(21) Appl. No.: 16/384,960

(22) Filed: Apr. 16, 2019

(65) Prior Publication Data
US 2020/0237952 A1 Jul. 30, 2020

(30) Foreign Application Priority Data
Jan. 24, 2019 (TW) ................ 108102773

(51) Int. Cl.
*A61L 9/20* (2006.01)
*B65D 21/08* (2006.01)
*B65B 55/02* (2006.01)

(52) U.S. Cl.
CPC ............ *A61L 9/20* (2013.01); *B65B 55/02* (2013.01); *B65D 21/086* (2013.01); *A61L 2202/23* (2013.01)

(58) Field of Classification Search
CPC .... A61L 9/20; A61L 2202/23; A61L 2202/11; A61L 2202/122; A61L 2/10; A61L 2/08; A61L 2/26; B65D 21/086; B65B 55/02; B65B 55/08
See application file for complete search history.

(56) References Cited

U.S. PATENT DOCUMENTS

| | | | |
|---|---|---|---|
| 4,210,073 A | 7/1980 | Weiss | |
| 6,576,190 B1 | 6/2003 | Park | |
| 7,654,402 B2 | 2/2010 | David et al. | |
| 8,141,956 B2 | 3/2012 | Schouten et al. | |
| 9,044,521 B2 | 6/2015 | Farren | |
| 9,839,707 B2 | 12/2017 | Won | |
| 2005/0108953 A1* | 5/2005 | Berdan | B60J 11/00 52/79.1 |
| 2010/0102252 A1 | 4/2010 | Harmon et al. | |
| 2010/0296968 A1 | 11/2010 | Cady | |
| 2011/0303659 A1 | 12/2011 | Perlman | |
| 2014/0031906 A1* | 1/2014 | Brezinski | A61N 5/06 607/90 |

(Continued)

FOREIGN PATENT DOCUMENTS

| | | |
|---|---|---|
| CN | 2817845 Y | 9/2006 |
| CN | 102535126 A | 7/2012 |

(Continued)

OTHER PUBLICATIONS

English translation of KR20130007326 (Year: 2013).*

*Primary Examiner* — Regina M Yoo
(74) *Attorney, Agent, or Firm* — CKC & Partners Co., LLC

(57) ABSTRACT

A sterilization device includes a sterilizing light source and an outer housing configured to accommodate and secure the sterilizing light source and shield light emitted by the sterilizing light source. The outer housing has a foldable structure to be selectively in an unfolded state or a folded state, wherein the outer housing in the unfolded state occupies a larger volume than that occupied by the outer housing in the folded state.

17 Claims, 12 Drawing Sheets

(56) References Cited

U.S. PATENT DOCUMENTS

| | | | |
|---|---|---|---|
| 2015/0367008 A1* | 12/2015 | Romo | A61L 2/24 |
| | | | 422/24 |
| 2017/0057841 A1 | 3/2017 | Blood et al. | |
| 2017/0216468 A1* | 8/2017 | Romo | A61L 2/10 |
| 2018/0140727 A1* | 5/2018 | Romo | A61L 2/24 |
| 2019/0038008 A1 | 2/2019 | Lee | |
| 2019/0365938 A1* | 12/2019 | Romo | A61L 9/20 |
| 2020/0069495 A1* | 3/2020 | Ballantyne | E04H 15/50 |

FOREIGN PATENT DOCUMENTS

| | | |
|---|---|---|
| CN | 204701890 U | 10/2015 |
| CN | 205095047 U | 3/2016 |
| CN | 205856047 U | 1/2017 |
| CN | 208319593 U | 1/2019 |
| EP | 1673609 B1 | 9/2014 |
| JP | H563494 U | 8/1993 |
| JP | 3000657 U | 8/1994 |
| JP | H9225012 A | 9/1997 |
| JP | 3043303 U | 11/1997 |
| JP | H11188081 A | 7/1999 |
| JP | 2002-142831 A | 5/2002 |
| JP | 3100836 U | 5/2004 |
| JP | 2009-050582 A | 3/2009 |
| JP | 2010-220984 A | 10/2010 |
| JP | 4803142 B2 | 10/2011 |
| KR | 20130026278 A | 3/2013 |
| KR | 20130006662 U | 11/2013 |
| KR | 20130007326 U | 12/2013 |
| TW | M467464 U | 12/2013 |
| TW | M531282 U | 11/2016 |
| TW | M567638 U | 10/2018 |
| WO | 2016003967 A1 | 1/2016 |

\* cited by examiner

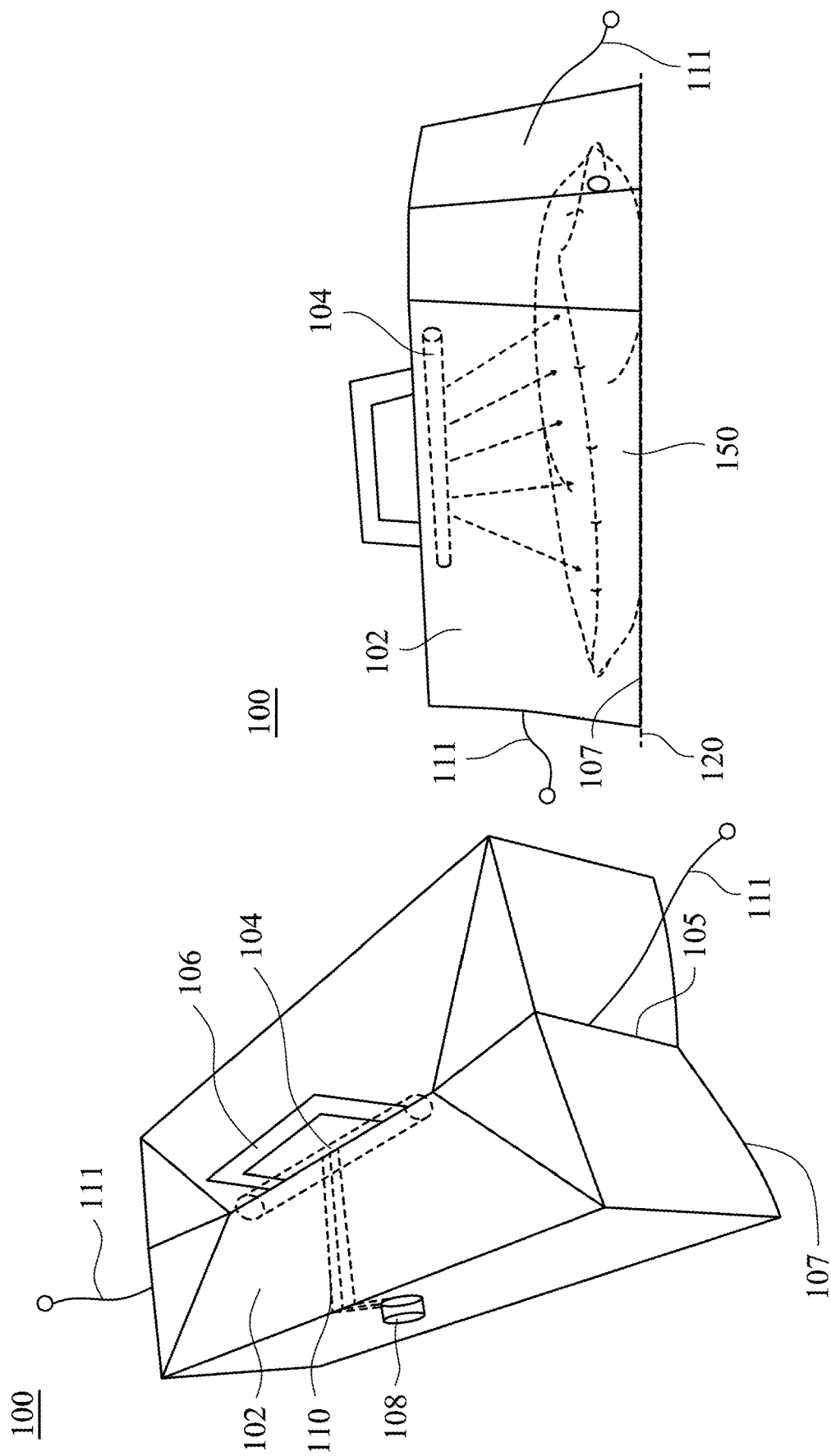

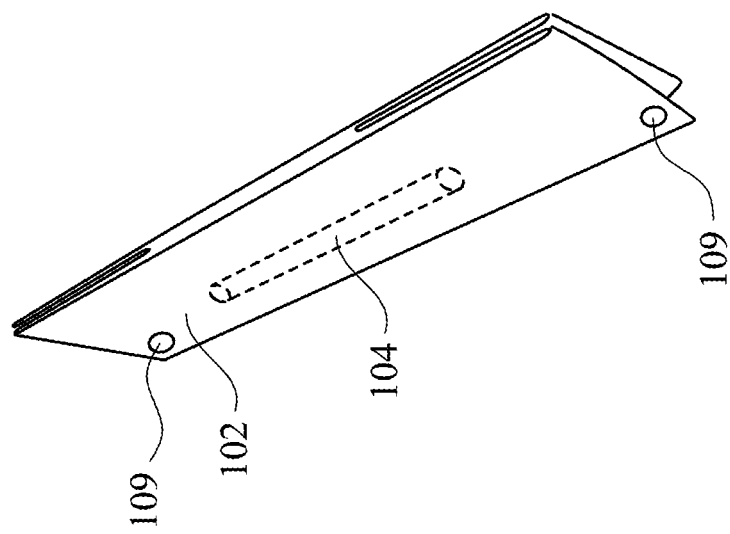
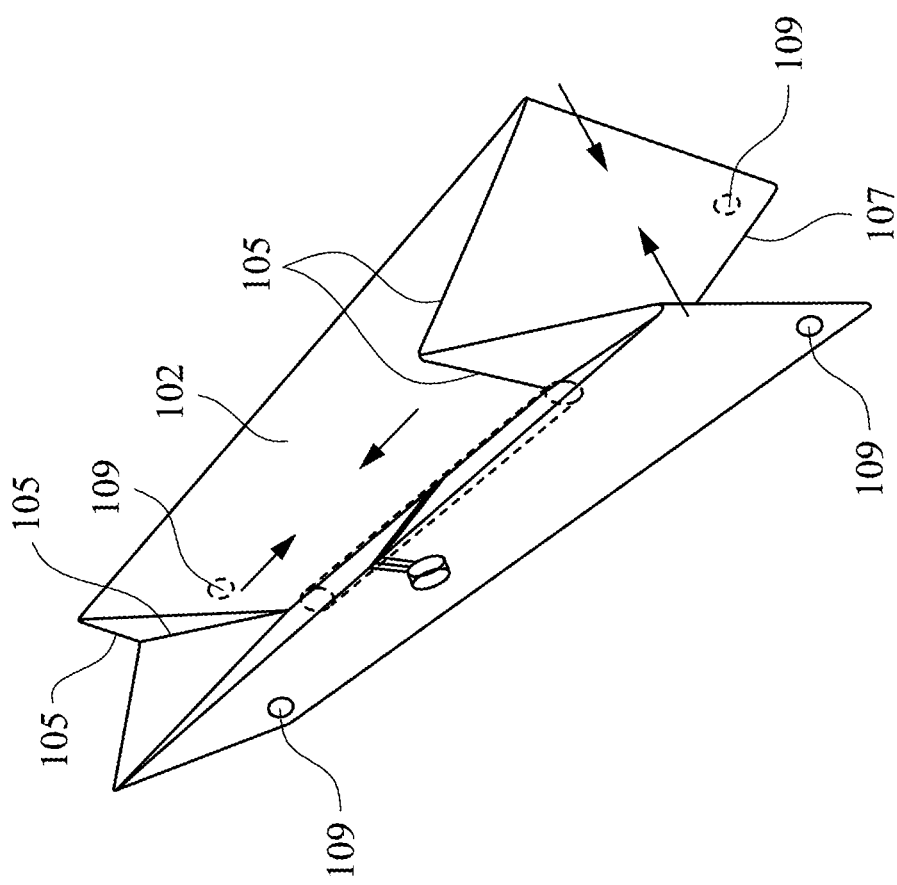
Fig. 5
Fig. 4

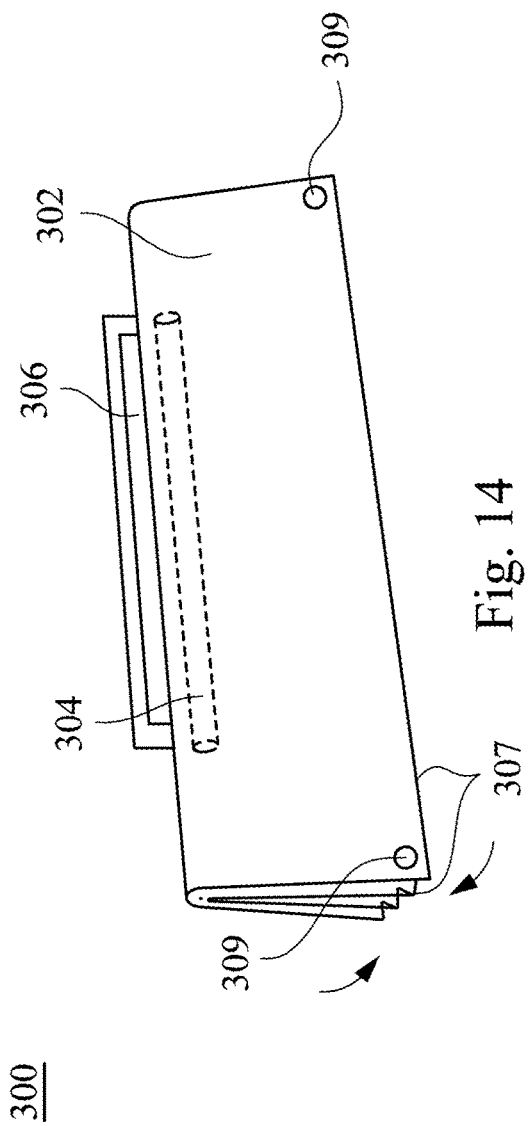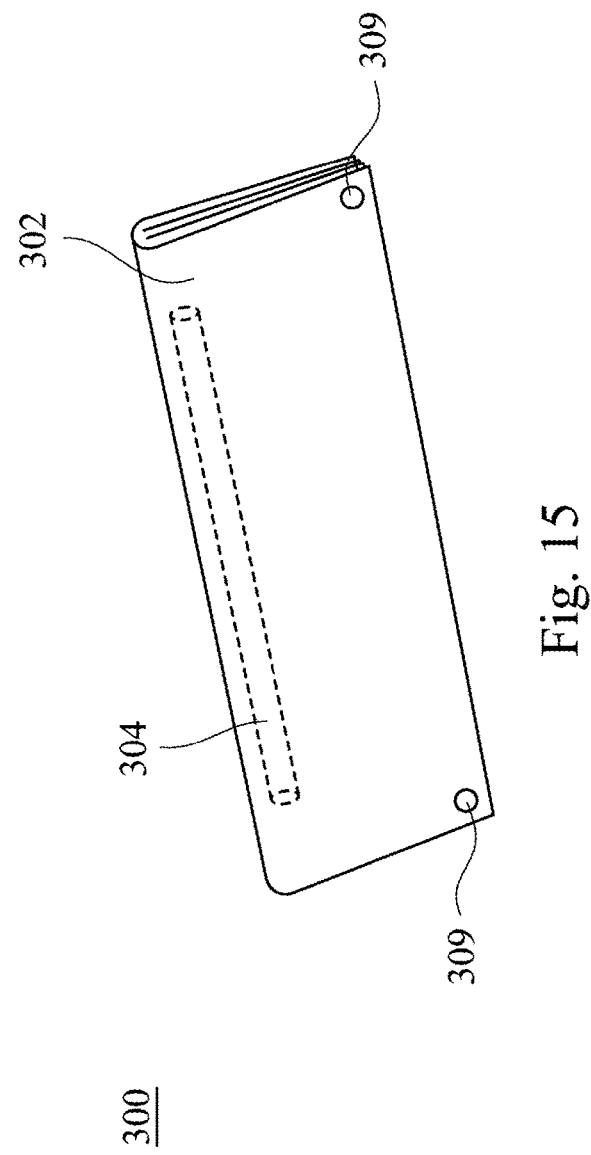
Fig. 14
Fig. 15

OPTICAL STERILIZATION DEVICE

CROSS-REFERENCE TO RELATED APPLICATION

This application claims priority to Taiwan Application Serial Number 108102773, filed Jan. 24, 2019 which is herein incorporated by reference.

BACKGROUND

Field of Invention

The present disclosure relates to a sterilization device, and more particularly, to an optical sterilization device.

Description of Related Art

The current ultraviolet sterilization products are all open light source or hand-held designs, which cannot isolate harmful ultraviolet light within a certain range and effectively sterilize such that it may cause health damage to users or people around.

SUMMARY

In one or more embodiments, a sterilization device includes a sterilizing light source and an outer housing configured to accommodate and secure the sterilizing light source and shield light emitted by the sterilizing light source. The outer housing has a foldable structure to be selectively in an unfolded state or a folded state, wherein the outer housing in the unfolded state occupies a larger volume than that occupied by the outer housing in the folded state.

In one or more embodiments, the outer housing has a bottom support edge in contact with a contact surface, the foldable structure has multiple fold lines, at least one of which extends to the bottom support edge.

In one or more embodiments, the sterilizing light source is an ultraviolet light source device.

In one or more embodiments, the outer housing in the unfolded state is configured to accommodate a sterilized object.

In one or more embodiments, the outer housing has a handle.

In one or more embodiments, the sterilization device further includes a controller configured to switch on or switch off the sterilizing light source.

In one or more embodiments, the sterilization device further includes a fastener configured to secure a structure of the outer housing in the unfolded state.

In one or more embodiments, the sterilization device further includes a detecting device configured to detect whether the outer housing is tilted in the unfolded state, wherein the detecting device is a vibration sensor or a tilt sensor.

In one or more embodiments, the foldable structure includes two symmetrical sub-fold structures that are symmetrical to each other relative to the handle.

In one or more embodiments, each of the two symmetrical sub-fold structures is a foldable sector structure.

In one or more embodiments, the sterilization device further includes multiple magnetic fasteners configured to secure a structure of the outer housing in the unfolded state or in the folded state.

In one or more embodiments, two sides of the outer housing each has a pull cord for a user to apply force to switch the outer housing from the folded state to the unfolded state.

In one or more embodiments, the unfolded state is achieved by simultaneously pulling two sides of the outer housing in the folded state.

In one or more embodiments, the folded state is achieved by simultaneously pushing two sides of the outer housing in the unfolded state.

In one or more embodiments, the unfolded state is achieved by simultaneously pulling the pull cords at two sides of the outer housing in the folded state.

In sum, the sterilization device of the present invention has a sterilizing light source and a foldable outer housing. The outer housing can be selectively in an unfolded state or a folded state, making the sterilized device in the folded state easy to carry and store. The opaque outer housing is used to shield the light emitted from the sterilizing light source to avoid light leakage and harm the surrounding people.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIG. 1 illustrates a perspective view of a sterilization device in a unfolded state according to a first embodiment of the present disclosure;

FIG. 2 illustrates a perspective view of a sterilization device sterilizing an object inside thereof according to the first embodiment of the present disclosure;

FIG. 4 illustrates how to fold a sterilization device from an unfolded state to a folded state according to the first embodiment of the present disclosure;

FIG. 5 illustrates a perspective view of a sterilization device in a folded state according to the first embodiment of the present disclosure;

FIG. 14 illustrates how to fold a sterilization device from an unfolded state to a folded state according to the third embodiment of the present disclosure;

FIG. 15 illustrates a perspective view of a sterilization device in a folded state according to the third embodiment of the present disclosure;

DETAILED DESCRIPTION

Figure 3:
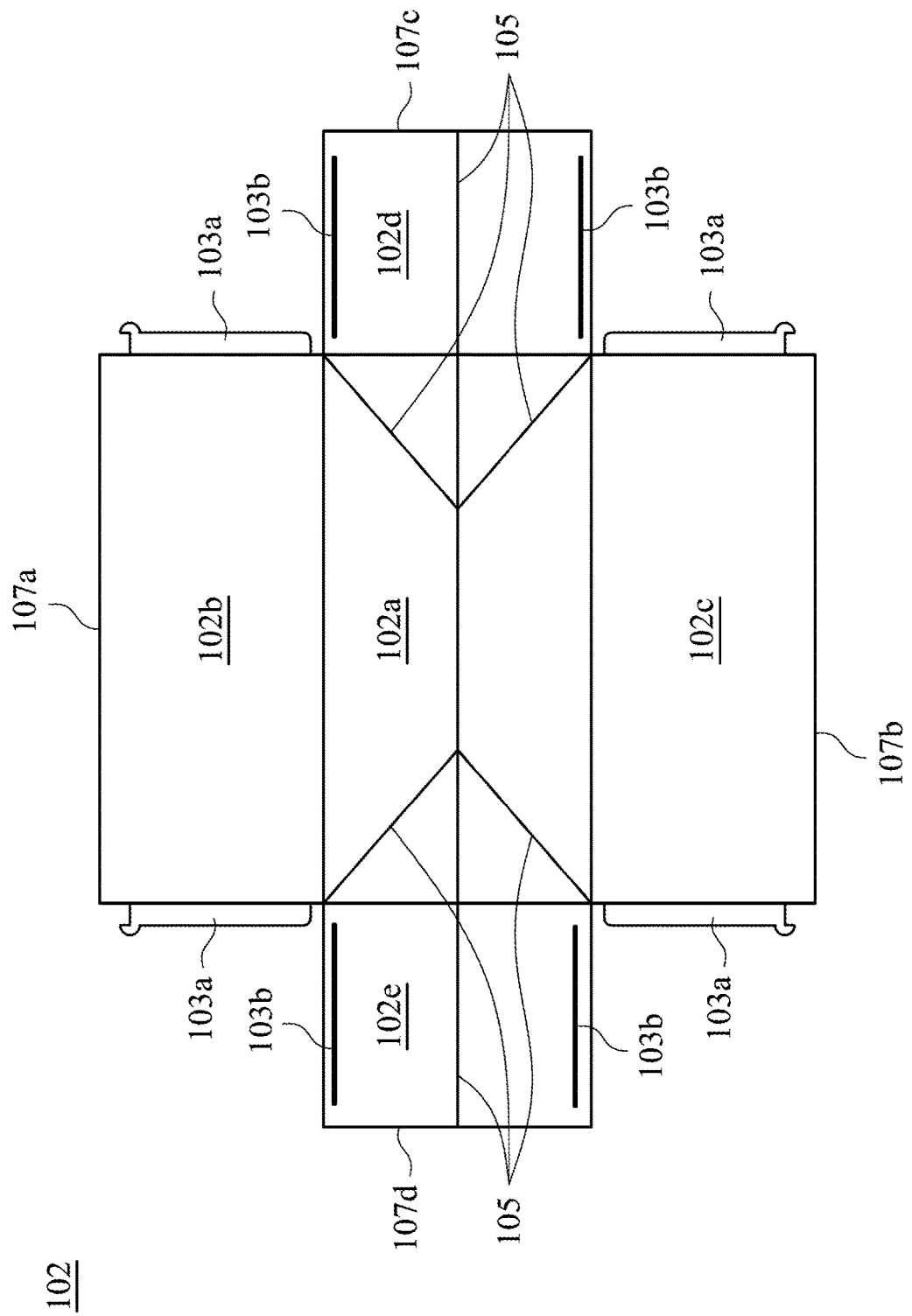
FIG. 3 illustrates an expanded view of an outer housing of a sterilization device according to the first embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

Reference is made to FIGS. 1 and 2. FIG. 1 illustrates a perspective view of a sterilization device in a unfolded state according to a first embodiment of the present disclosure, and FIG. 2 illustrates a perspective view of a sterilization device sterilizing an object inside thereof according to the first embodiment of the present disclosure. A sterilization device 100 includes a sterilizing light source 104 and an outer housing 102. The outer housing 102 is used to receive and fix the sterilizing light source 104 and to shield the light emitted by the sterilizing light source 104. The outer housing 102 has a foldable structure to be selectively in an unfolded state or a folded state. A user can simultaneously pull the two sides of the outer housing 102 to expand the foldable structure to achieve the unfolded state, or simultaneously compress or push the two sides of the outer housing 102 to fold the foldable structure to achieve the folded state. The volume occupied by the outer housing 102 in the unfolded state is larger than the volume occupied by the outer housing 102 in the folded state (for example, the state shown in FIG. 5), so that the sterilization device 100 is easy to store and carry. Each side of the outer housing 102 may be provided with a pull cord 111 for the user to grasp the pull cord and simultaneously apply force to facilitate the outer housing 102 to switch from the folded state to the unfolded state.

The sterilizing light source 104 may be an ultraviolet light source device or other sterilizing light source device. The sterilizing light source 104 is fixed in an accommodation space formed by the outer housing 102 under the unfolded state. When the sterilization device 100 is used, a bottom support edge 107 of the outer housing 102 is joined to a contact surface or a support surface 120 so that the light emitted by the sterilizing light source 104 is prevented from leaking and damaging the surrounding personnel. The accommodation space of the outer housing 102 in the unfolded state is used to accommodate a sterilized object 150, and the light emitted by the sterilizing light source 104 kills the bacteria or virus on the sterilized object 150.

The outer housing 102 has a handle 106 to be easily carried and stored. The sterilization device 100 also includes a controller 108 connected to the sterilizing light source 104 via a conductive path 110. In some embodiments, the controller 108 is used to switch on or switch off the sterilizing light source 104. In some embodiments, the controller 108 can include or be a detecting device for detecting whether the outer housing in an unfolded state is tilted or inverted, wherein the detecting device may be a vibration sensor or a tilt sensor. When the detecting device detects that the outer housing 102 is tilted in the unfolded state, the sterilizing light source 104 will be turned off and the light emitted by the sterilizing light source 104 is prevented from leaking and damaging the surrounding personnel.

Reference is made to FIG. 3, which illustrates an expanded view of an outer housing of a sterilization device according to the first embodiment of the present disclosure. An expanded sheet of the outer housing 102 includes a plurality of sections (102a, 102b, 102c, 102d, 102e), and four sides of the middle section 102a connect the remaining sections (102b, 102c, 102d, 102e) to form an outer housing. Each section (102b, 102c) has a latch piece 103a on both sides, and each section (102d, 102e) has a slit 103b on both sides. After the sections (102b, 102c, 102d, 102e) is bent toward the section 102a, the corresponding piece 103a is inserted into the corresponding slit 103b to assemble the outer housing 102, and outer edges (107a, 107b, 107c, 107d) of each section (102b, 102c, 102d, 102e) are joined to form a bottom support edge 107.

Reference is made to FIGS. 4 and 5. FIG. 4 illustrates how to fold a sterilization device from an unfolded state to a folded state according to the first embodiment of the present disclosure, and FIG. 5 illustrates a perspective view of a sterilization device in a folded state according to the first embodiment of the present disclosure.

The outer housing 102 in the folded state is achieved by bending the outer housing 102 in the unfolded state in the direction of the arrow in the figure by along plural fold lines 105 of the foldable structure. In the present embodiment, two of the fold lines 105 extend to the bottom support edge 107. In some embodiments, the outer housing 102 can include a plurality of magnetic fasteners 109 to secure a structure of the outer housing 102 in the folded state, making it easier to carry and store.

Figure 7:
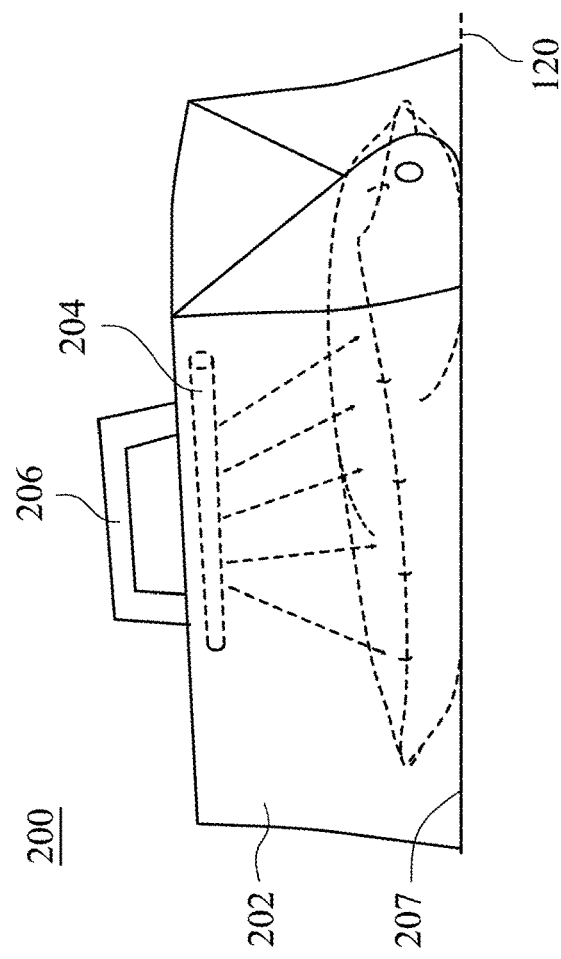
FIG. 7 illustrates a perspective view of a sterilization device sterilizing an object inside thereof according to the second embodiment of the present disclosure.
Figure 6:
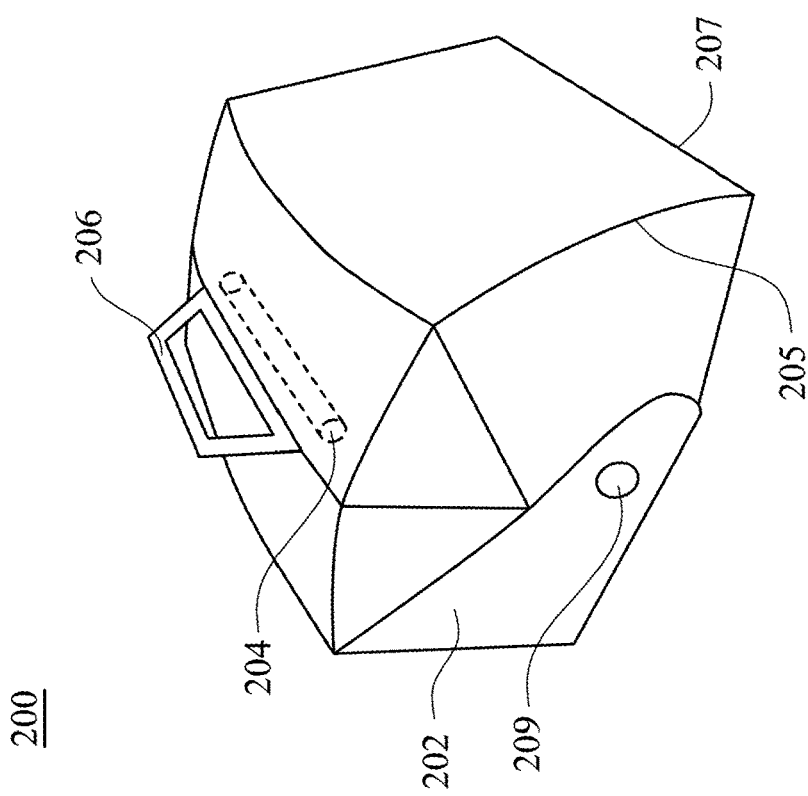
FIG. 6 illustrates a perspective view of a sterilization device in a unfolded state according to a second embodiment of the present disclosure.

Reference is made to FIGS. 6 and 7. FIG. 6 illustrates a perspective view of a sterilization device in a unfolded state according to a second embodiment of the present disclosure, and FIG. 7 illustrates a perspective view of a sterilization device sterilizing an object inside thereof according to the second embodiment of the present disclosure. A sterilization device 200 includes a sterilizing light source 204 and an outer housing 202. The outer housing 202 is configured to receive and fix the sterilizing light source 204 and to shield the light emitted by the sterilizing light source 204. The outer housing 202 has a foldable structure to be selectively in an unfolded state or a folded state. The volume occupied by the outer housing 202 in the unfolded state is larger than the volume occupied by the outer housing 202 in the folded state (for example, the state shown in FIG. 10), so that the sterilization device 200 is easy to store and carry.

The sterilizing light source 204 may be an ultraviolet light source device or other sterilizing light source device. The sterilizing light source 204 is fixed in the accommodation space formed by the outer housing 202 in the unfolded state.

When the sterilization device 200 is used, the bottom support edge 207 of the outer housing 202 is joined to a contact surface or a support surface 120 so that the light emitted by the sterilizing light source 204 is prevented from leaking and damaging the surrounding personnel. The accommodation space of the outer housing 202 in the unfolded state is used to accommodate a sterilized object 150, and the light emitted by the sterilizing light source 204 kills the bacteria or virus of the sterilized object 150. The outer housing 202 has a fastener 209 for securing the structure of the outer housing 202 in the unfolded state. In some embodiments, the fastener 209 may be a magnetic fastener and can be used to secure a structure of the outer housing 202 in the folded state.

The outer housing 202 has a handle 206 that makes it easy to carry. The sterilization device 200 may also include a controller with similar designs and functions of the aforementioned controller 108.

Figure 8:
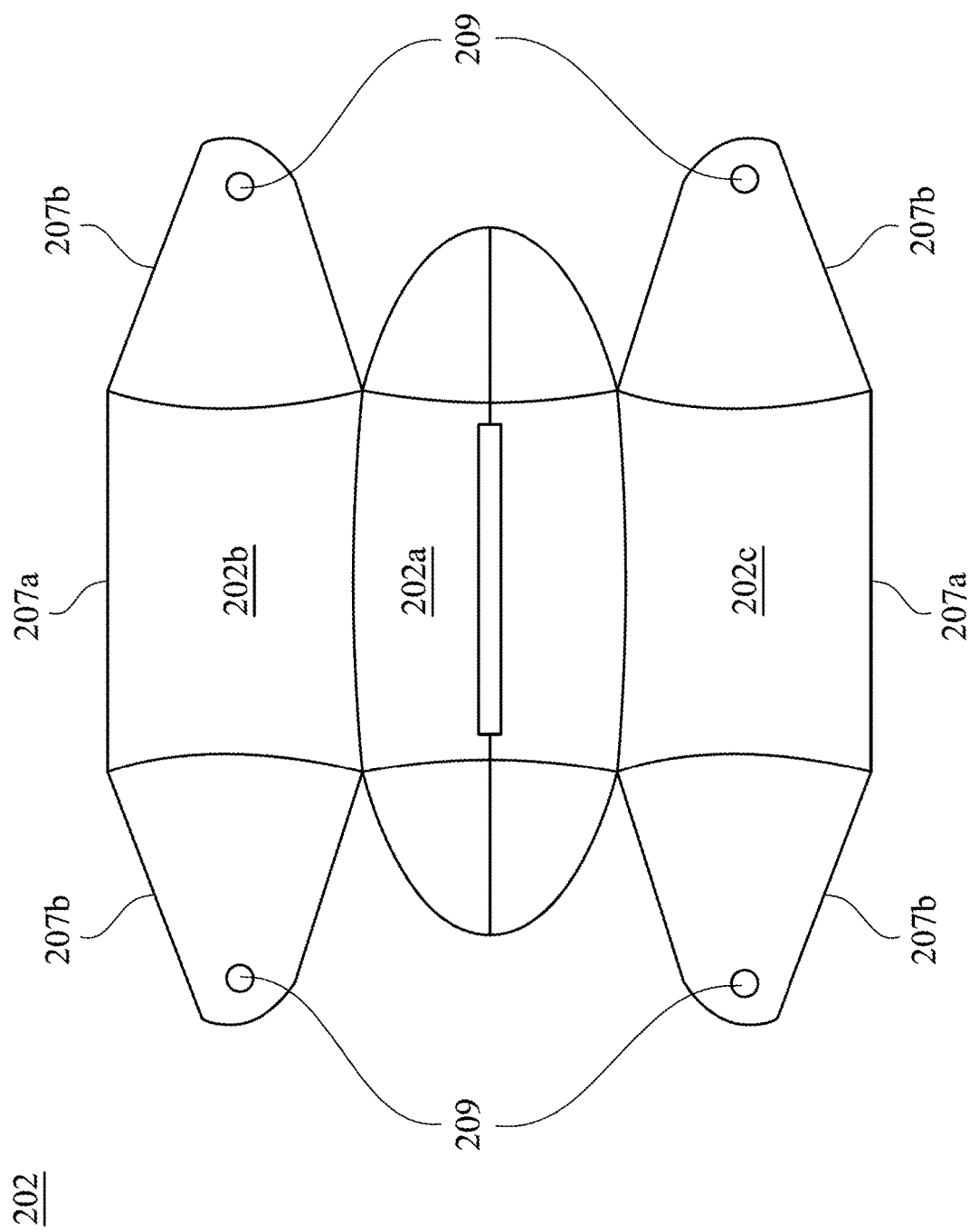
FIG. 8 illustrates an expanded view of an outer housing of a sterilization device according to the second embodiment of the present disclosure.

Reference is made to FIG. 8, which illustrates an expanded view of an outer housing of a sterilization device according to the second embodiment of the present disclosure. An expanded sheet of the outer housing 202 includes a plurality of sections (202a, 202b, 202c), and the sections (202b, 202c) are connected to two sides of the intermediate section 202a to form an outer housing. Each section (202b, 202c) has a fastener 209 on both sides. After the sections (202b, 202c) are bent toward the section 202a, the outer housings 202 are assembled by engaging corresponding pairs of fasteners 209, and the outer edges (207a, 207b) of the sections (202b, 202c) are joined to form a bottom support edge 207.

Figure 10:
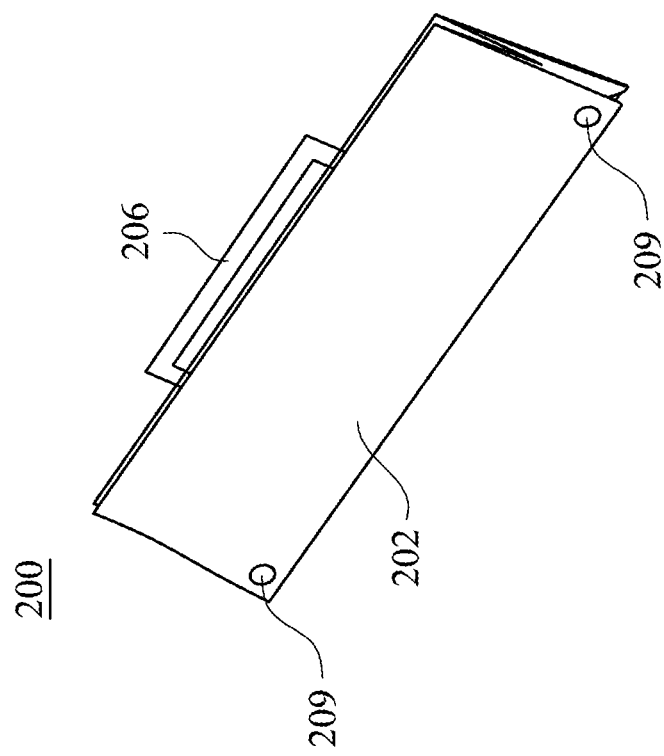
FIG. 10 illustrates a perspective view of a sterilization device in a folded state according to the second embodiment of the present disclosure.
Figure 9:
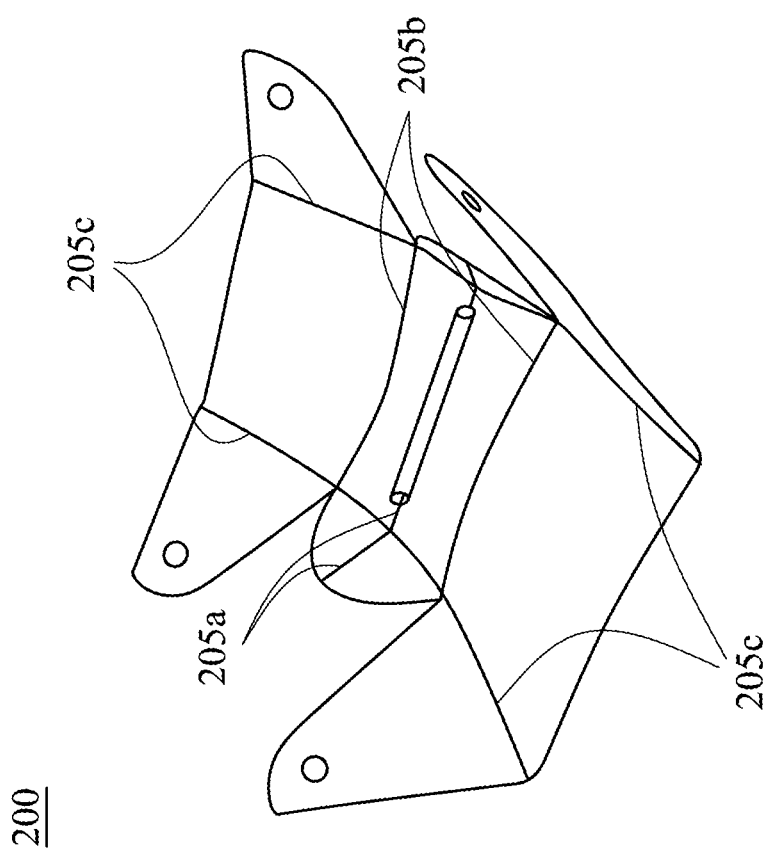
FIG. 9 illustrates how to fold a sterilization device from an unfolded state to a folded state according to the second embodiment of the present disclosure.

Reference is made to FIGS. 9 and 10. FIG. 9 illustrates how to fold a sterilization device from an unfolded state to a folded state according to the second embodiment of the present disclosure, and FIG. 10 illustrates a perspective view of a sterilization device in a folded state according to the second embodiment of the present disclosure.

The outer housing 202 with fasteners unlocked or released is folded into the folded state by the plural fold lines (205a, 205b, 205c) of the foldable structure along the direction of the arrow in the figure. In the present embodiment, four of the plural fold lines (e.g., fold line 205c) extend to the bottom support edge 207.

Figure 11:
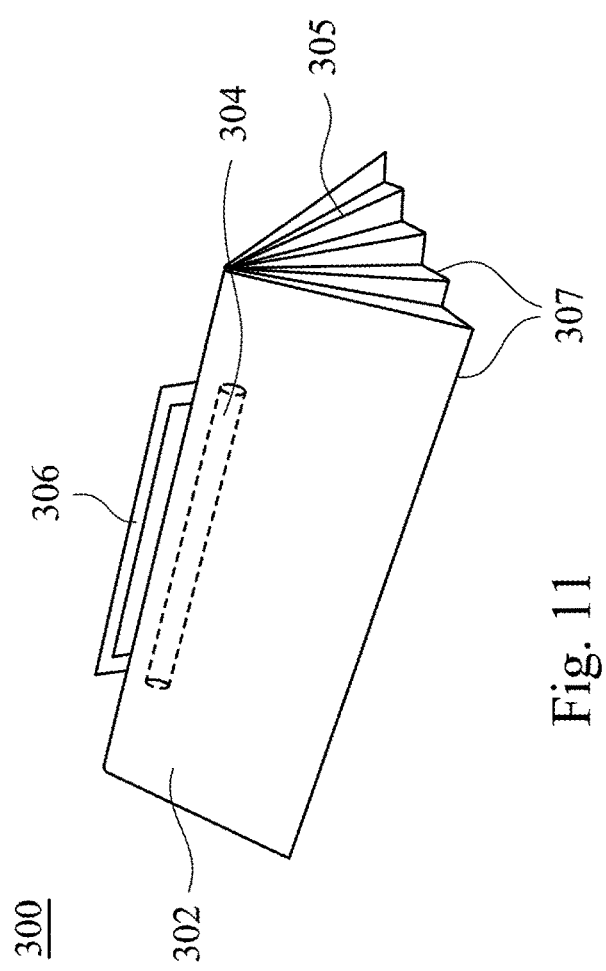
FIG. 11 illustrates a perspective view of a sterilization device in a unfolded state according to a third embodiment of the present disclosure.
Figure 12:
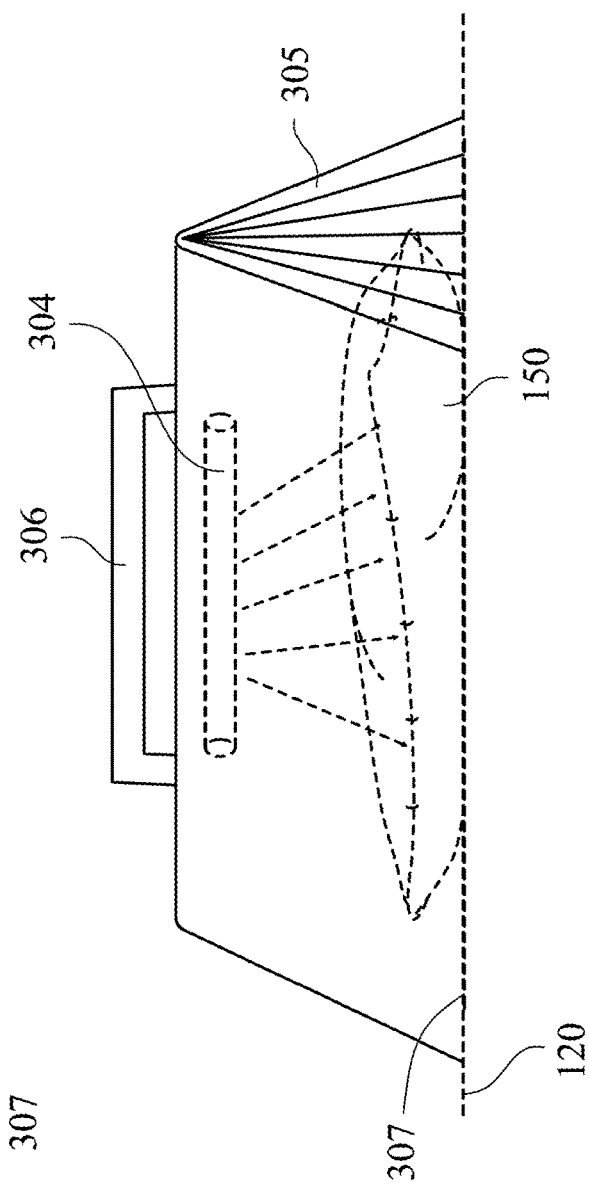
FIG. 12 illustrates a perspective view of a sterilization device sterilizing an object inside thereof according to the third embodiment of the present disclosure.

Reference is made to FIGS. 11 and 12. FIG. 11 illustrates a perspective view of a sterilization device in an unfolded state according to a third embodiment of the present disclosure, and FIG. 12 illustrates a perspective view of a sterilization device sterilizing an object inside thereof according to the third embodiment of the present disclosure. A sterilization device 300 includes a sterilizing light source 304 and an outer housing 302. The outer housing 302 is used to receive and fix the sterilizing light source 304 and to shield the light emitted by the sterilizing light source 304. The outer housing 302 has a foldable structure (e.g., multiple fold lines 305) that is selectively in an unfolded state or a folded state. The volume occupied by the outer housing 302 in the unfolded state is larger than the volume occupied by the outer housing 302 in the folded state (for example, the state shown in FIG. 15), so that the sterilization device 300 is easy to store and carry.

The sterilizing light source 304 may be an ultraviolet light source device or other sterilizing light source device. The sterilizing light source 304 is fixed in the accommodation space formed by the outer housing 302 under the unfolded state. When the sterilization device 300 is used, the bottom support edge 307 of the outer housing 302 is joined to a contact surface or a support surface 120, so that the light emitted by the sterilizing light source 304 is prevented from leaking and damaging the surrounding personnel. The accommodation space of the outer housing 302 in the unfolded state is used to accommodate a sterilized object 150, and the light emitted by the sterilizing light source 304 kills the bacteria or virus of the sterilized object 150.

The outer housing 302 has a handle 306 that makes it easy to carry. The sterilization device 300 also includes a controller similar to the aforementioned controller 108 in its design and function.

Figure 13:
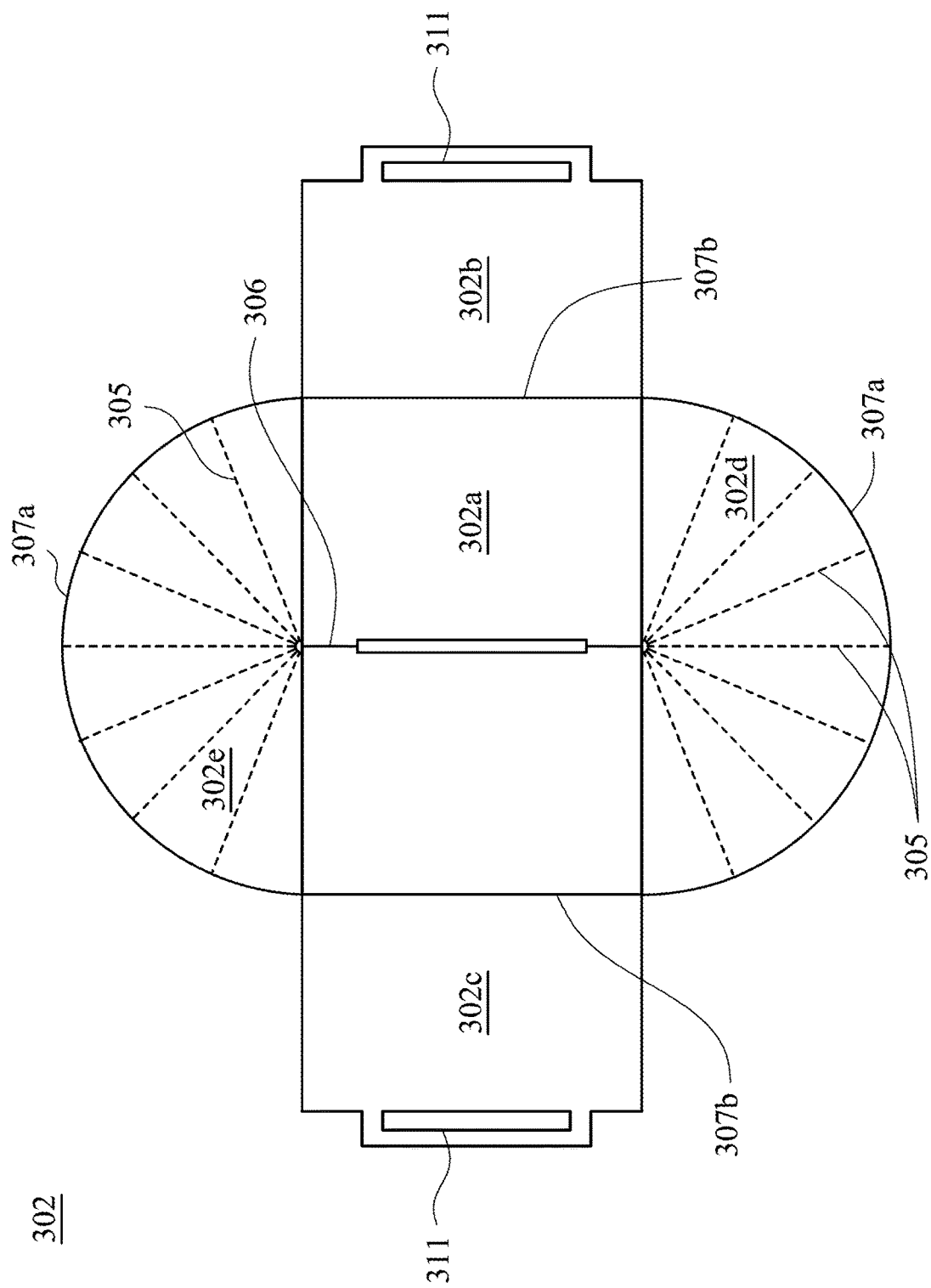
FIG. 13 illustrates an expanded view of an outer housing of a sterilization device according to the first embodiment of the present disclosure.

Reference is made to FIG. 13 which illustrates an expanded view of an outer housing of a sterilization device according to the first embodiment of the present disclosure. An expended sheet of the outer housing 302 includes a plurality of sections (302a, 302b, 302c, 302d, 302e), and the four sides of the middle section 302a connect the remaining sections (302b, 302c, 302d, 302e) to form an outer housing. The outer side of each section (302b, 302c) has a latch piece 311. When the intermediate section 302a is bent towards the middle fold line 306, the two latch pieces 311 are fastened to each other to assemble the outer housing 302, and the outer edge 307a of the section (302d, 302e) and the inner edge 307b of the section (302b, 302c) are joined to form a bottom support edge 307.

Reference is made to FIGS. 14 and 15. FIG. 14 illustrates how to fold a sterilization device from an unfolded state to a folded state according to the third embodiment of the present disclosure, and FIG. 15 illustrates a perspective view of a sterilization device in a folded state according to the third embodiment of the present disclosure. The folded structure of the outer housing 302 includes two symmetric sub-fold structures, e.g., foldable sectors, that are symmetric with each other relative to the handle 306. The outer housing 302 in the unfolded state is folded to the outer housing 302 in the folded state by a plurality of fold lines 305 in the direction of the arrow in the figure. In this embodiment, the plurality of fold lines 305 all extend to the bottom support edge 307. In some embodiments, the outer housing 302 may include a plurality of magnetic fasteners 309 to secure a structure of the outer housing 302 in a folded state, thereby making it easier to carry and store.

Figure 16:
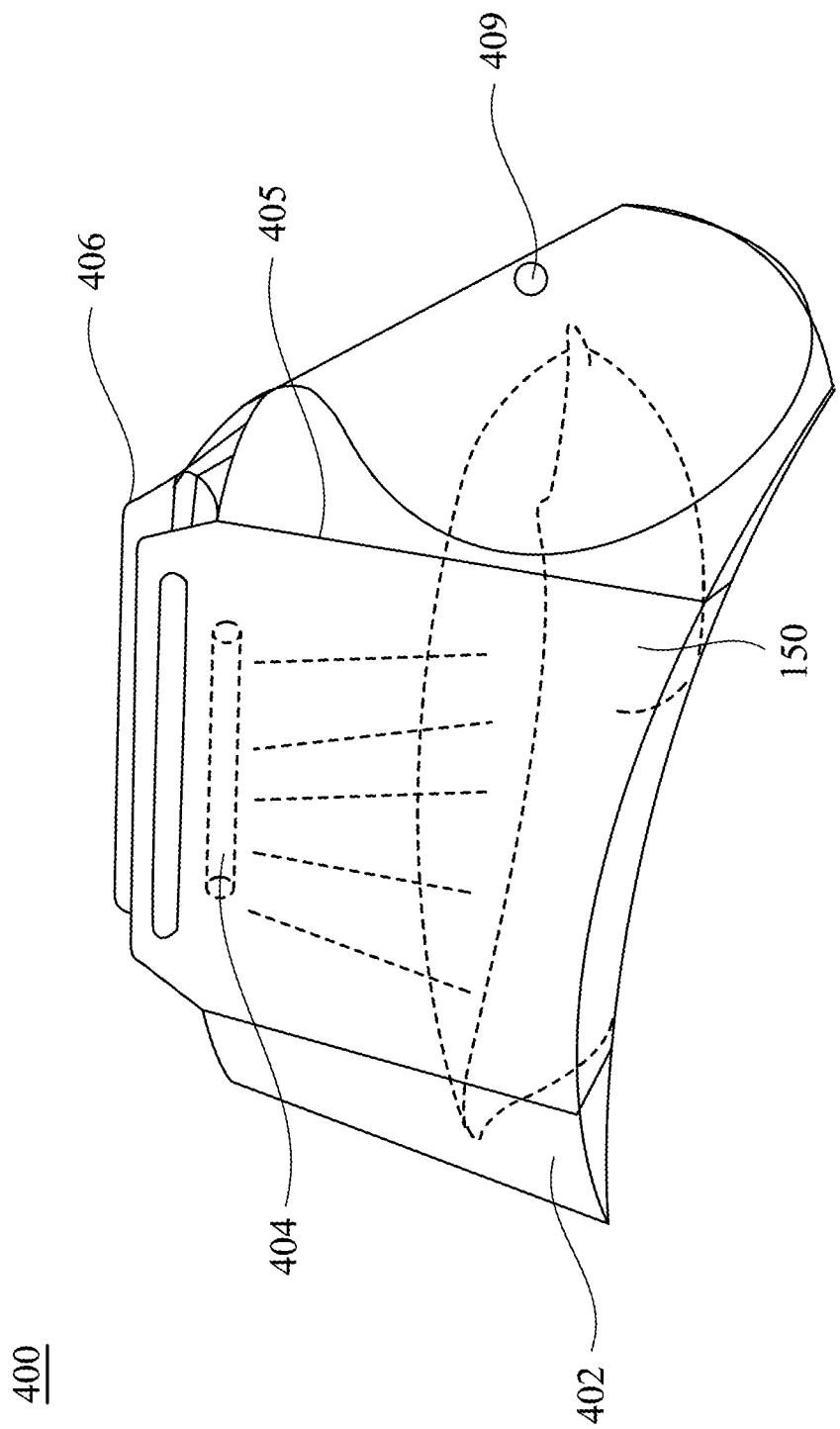
FIG. 16 illustrates a perspective view of a sterilization device sterilizing an object inside thereof according to the fourth embodiment of the present disclosure.

Reference is made to FIG. 16 illustrates a perspective view of a sterilization device sterilizing an object inside thereof according to the fourth embodiment of the present disclosure. A sterilization device 400 includes a sterilizing light source 404 and an outer housing 402. The outer housing 402 is used to receive and fix the sterilizing light source 404 and to shield the light emitted by the sterilizing light source 404. The outer housing 402 has a foldable structure (e.g., multiple fold lines 405) that is selectively in an unfolded state or a folded state. The volume occupied by the outer housing 402 in the unfolded state is larger than the volume occupied by the outer housing 402 in the folded state (such as the state depicted in FIG. 20), thereby making the sterilization device 400 easy to store and carry.

The sterilizing light source 404 may be an ultraviolet light source device or other sterilizing light source device. The sterilizing light source 404 is fixed in the accommodation space formed by the outer housing 402 under the unfolded state. When the sterilization device 400 is used, the outer housing 402 is placed on a contact surface or a bearing surface. The accommodation space of the outer housing 402 in the unfolded state is used to accommodate a sterilized object 150, and the light emitted by the sterilizing light source 404 kills the bacteria or virus of the sterilized object 150.

The outer housing 402 has a handle 406 that makes it easy to carry. The sterilization device 400 also includes a controller similar to the design and functionality of the aforementioned controller 108.

Figure 18:
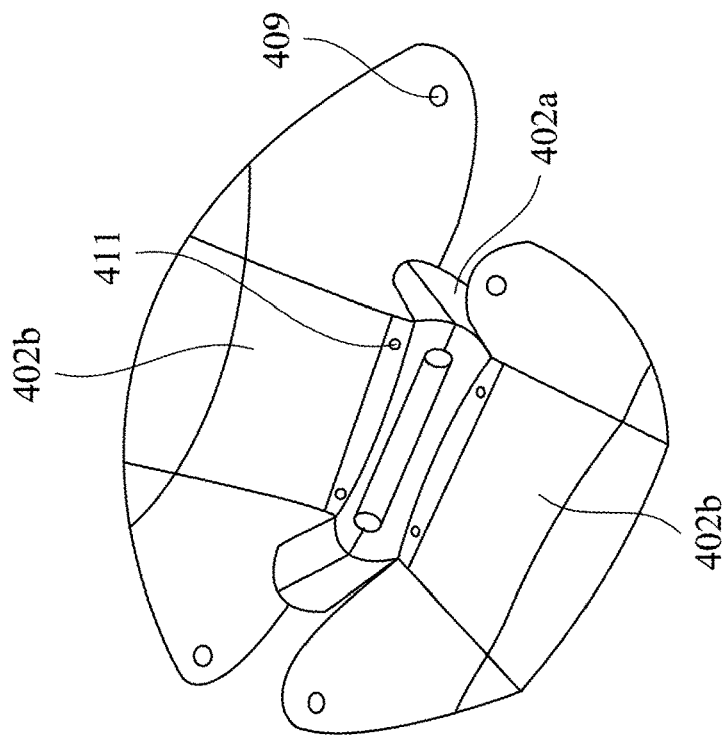
FIG. 18 illustrates how to assemble an outer housing of a sterilization device according to the fourth embodiment of the present disclosure.
Figure 17:
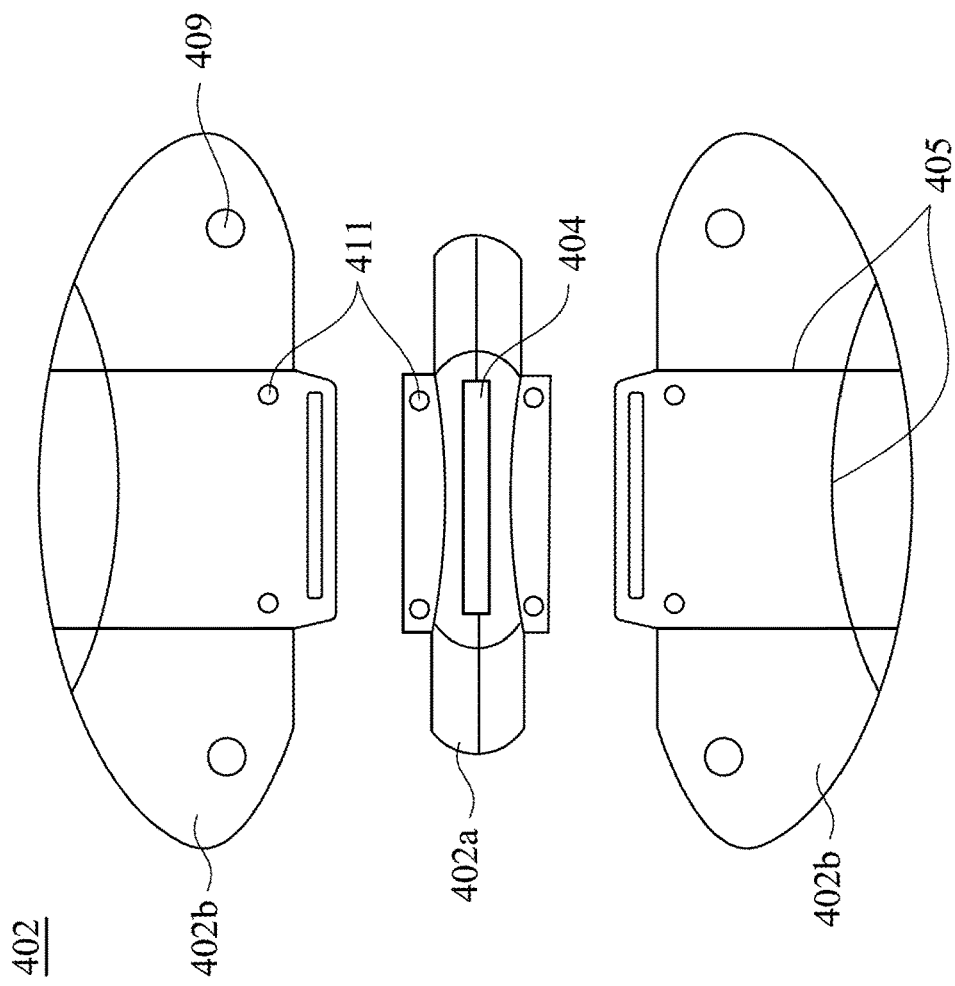
FIG. 17 illustrates an exploded view of an outer housing of a sterilization device according to the fourth embodiment of the present disclosure.

Reference is made to FIGS. 17 and 18. FIG. 17 illustrates an exploded view of an outer housing of a sterilization device according to the fourth embodiment of the present disclosure, and FIG. 18 illustrates how to assemble an outer housing of a sterilization device according to the fourth embodiment of the present disclosure.

This embodiment differs from the foregoing embodiment mainly in that each section (402a, 402b) of the outer housing 402 is not integrally formed but separately manufactured, and then connection members 411 are bonded or engaged with each other to achieve a status as shown in FIG. 18. The outer side of each section 402b of the outer housing 402 has a magnetic fastener 409. When the outer housing 402 is bent into the unfolded state as shown in FIG. 16, the magnetic fasteners 409 are fastened to each other to secure a structure of the outer housing in the unfolded state.

Figure 20:
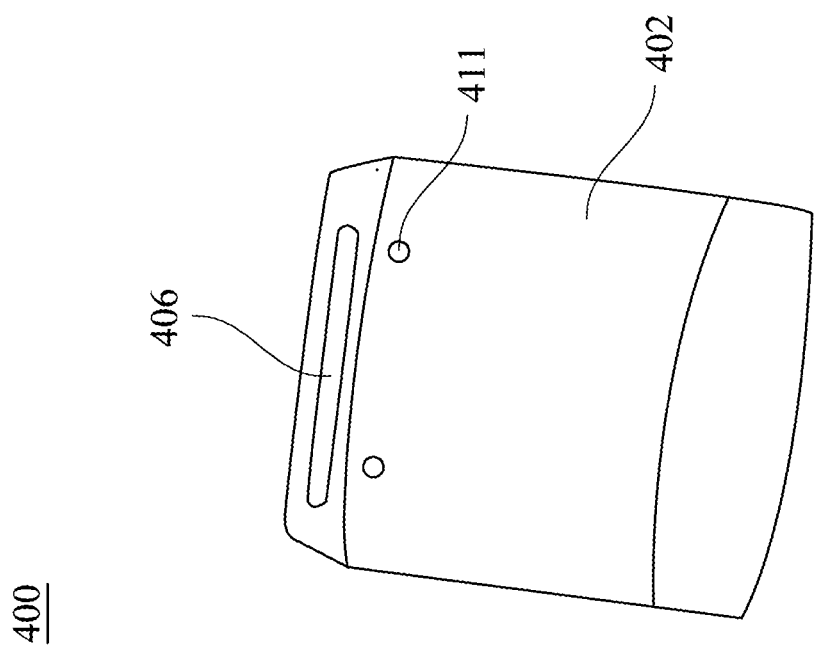
FIG. 20 illustrates a perspective view of a sterilization device in a folded state according to the fourth embodiment of the present disclosure.
Figure 19:
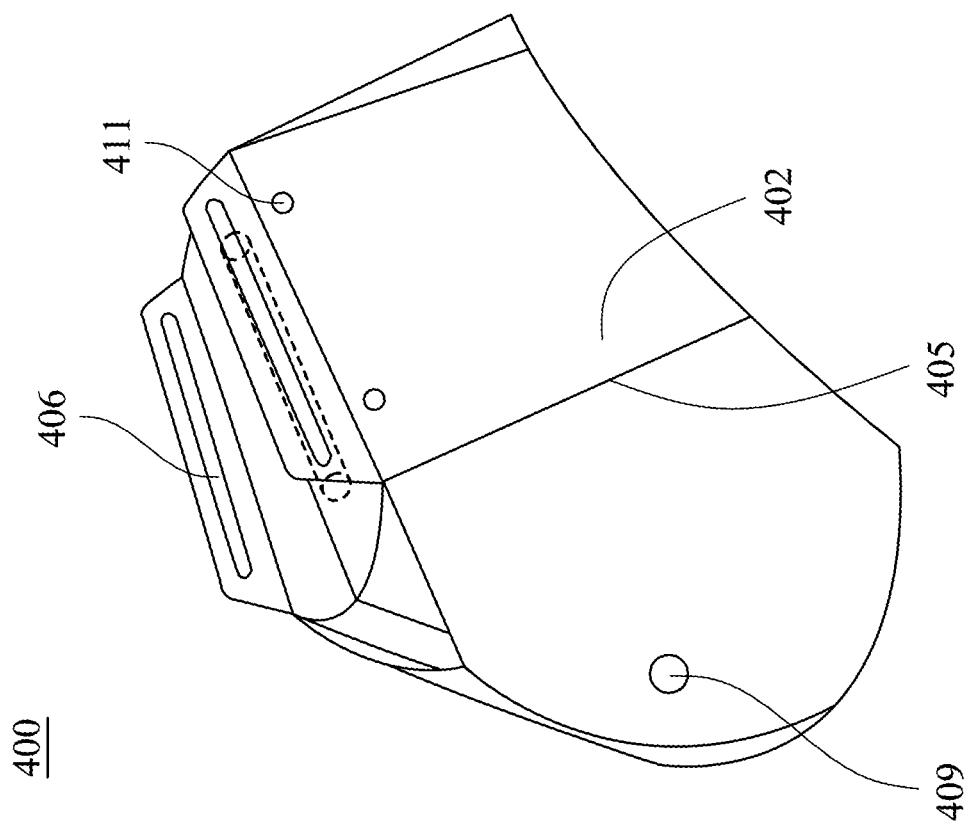
FIG. 19 illustrates how to fold a sterilization device from an unfolded state to a folded state according to the fourth embodiment of the present disclosure.

Reference is made to FIGS. 19 and 20. FIG. 19 illustrates how to fold a sterilization device from an unfolded state to a folded state according to the fourth embodiment of the present disclosure, and FIG. 20 illustrates a perspective view of a sterilization device in a folded state according to the fourth embodiment of the present disclosure. When the sterilization device 400 needs to be stored or carried, the outer housing 402 can be bent along its fold line 405 into a folded state as shown in FIG. 20 to facilitate carrying and storage. The magnetic fasteners 409 may also be fastened to each other to secure a structure of the outer housing in the folded state.

In sum, the sterilization device of the present invention has a sterilizing light source and a foldable outer housing. The outer housing can be selectively in an unfolded state or a folded state, making the sterilized device in the folded state easy to carry and store. The opaque outer housing is used to shield the light emitted from the sterilizing light source to avoid light leakage and harm the surrounding people.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A sterilization device comprising:
    a sterilizing light source; and
    an outer housing configured to accommodate and secure the sterilizing light source and shield light emitted by the sterilizing light source, the outer housing consists of a single-piece foldable structure to be selectively in an unfolded state or a folded state, wherein the outer housing in the unfolded state occupies a larger volume than that occupied by the outer housing in the folded state, wherein the single-piece foldable structure comprises an intermediate oval-shaped section, a first section and a second section, the first section and the second section are connected to two opposite sides of the intermediate oval-shaped section respectively, a portion of the first and second sections are joined to form a portion of a bottom support edge when the outer housing is in an assembled state.

2. The sterilization device of claim 1, wherein the single-piece foldable structure has multiple fold lines, at least one of which extends to the bottom support edge.

3. The sterilization device of claim 1, wherein the outer housing in the unfolded state is configured to accommodate a sterilized object.

4. The sterilization device of claim 1, wherein the outer housing has a handle.

5. The sterilization device of claim 4, wherein the single-piece foldable structure comprises two symmetrical sub-fold structures that are symmetrical to each other relative to the handle.

6. The sterilization device of claim 5, wherein each of the two symmetrical sub-fold structures is a foldable sector structure.

7. The sterilization device of claim 1, further comprising a controller configured to switch on or switch off the sterilizing light source.

8. The sterilization device of claim 1, further comprising a fastener configured to secure a structure of the outer housing in the unfolded state.

9. The sterilization device of claim 1, further comprising a detecting device configured to detect whether the outer housing is tilted in the unfolded state, wherein the detecting device is a vibration sensor or a tilt sensor.

10. The sterilization device of claim 1, further comprising multiple magnetic fasteners configured to secure a structure of the outer housing in the unfolded state or in the folded state.

11. The sterilization device of claim 1, wherein two sides of the outer housing each has a pull cord for a user to apply force to switch the outer housing from the folded state to the unfolded state.

12. The sterilization device of claim 11, wherein the unfolded state is achieved by simultaneously pulling the pull cords at the two sides of the outer housing in the folded state.

13. The sterilization device of claim 1, wherein the unfolded state is achieved by simultaneously pulling two sides of the outer housing in the folded state.

14. The sterilization device of claim 1, wherein the folded state is achieved by simultaneously pushing two sides of the outer housing in the unfolded state.

15. The sterilization device of claim 1, wherein the intermediate oval-shaped section has a major axis and a minor axis, and the sterilizing light source is secured to the intermediate oval-shaped section and extends substantially along the major axis of the intermediate oval-shaped section.

16. The sterilization device of claim 1, wherein:
    the intermediate oval-shaped section has a major axis and a minor axis;
    the first section has a first inner edge and a first outer edge that are opposite to each other, and the second section has a second inner edge and a second outer edge that are opposite to each other;
    the first section is connected to the intermediate oval-shaped section at the first inner edge, and the second section is connected to the intermediate oval-shaped section at the second inner edge;
    the first section comprises a first middle section between the first inner edge and the first outer edge, and two first outer sections extending outwardly in opposite directions from the first middle section; and
    the second section comprises a second middle section between the second inner edge and the second outer edge, and two second outer sections extending outwardly in opposite directions from the second middle section.

17. The sterilization device of claim 16, wherein a fastener is disposed at an end portion of each of the two first outer sections and the two second outer sections, and the fastener on one of the two first outer sections and the fastener on an opposing one of the two second outer sections are connected to each other when the outer housing is in the assembled state.

* * * * *